United States Patent [19]

Bonne et al.

[11] Patent Number: 5,235,844
[45] Date of Patent: Aug. 17, 1993

[54] MULTIPLE GAS PROPERTY SENSOR

[75] Inventors: Ulrich Bonne, Hopkins; Robert J. Matthys, Minneapolis; David Kubisiak, Chanhassen, all of Minn.

[73] Assignee: Niagara Mohawk Power Corporation, Syracuse, N.Y.

[21] Appl. No.: 781,770

[22] Filed: Oct. 23, 1991

[51] Int. Cl.[5] .......................................... G01N 29/02
[52] U.S. Cl. ..................................... 73/24.01; 374/36
[58] Field of Search ................ 73/24.01, 24.05, 32 A; 374/36

[56] References Cited

U.S. PATENT DOCUMENTS

| | | | |
|---|---|---|---|
| 3,120,750 | 2/1964 | Root, III | 73/24.01 |
| 3,420,092 | 1/1969 | Dorsch | 73/32 |
| 3,879,992 | 4/1975 | Bartera | 73/24.01 |
| 4,177,669 | 12/1979 | Wenger . | |
| 4,384,792 | 5/1983 | Sommers et al. | 374/36 |
| 4,429,564 | 2/1984 | Ideda et al. | 73/32 A |
| 4,644,803 | 2/1987 | Ward | 73/862.581 |
| 4,734,609 | 3/1988 | Jasmine | 310/315 |
| 4,783,168 | 11/1988 | Florisson et al. | 356/301 |
| 4,885,938 | 12/1989 | Higashi | 73/204.18 |
| 4,944,035 | 7/1990 | Aagardl et al. | 364/556 |
| 4,956,793 | 9/1990 | Bonne et al. | 364/558 |

FOREIGN PATENT DOCUMENTS

140249  11/1981  Japan .................................. 73/24.01

OTHER PUBLICATIONS

Frishe, Richard, "Vibratory Pressure Sensors", Scientific Honeyweller, pp. 79–84, Fall, 1987.
Sullivan, John J., "Development of Variable Capacitance Pressure Transducers for Vacuum Applns.", Vacuum Science Technology, pp. 1721–1730, May/Jun., 1985.
Ono et al., "Design and Testing of Quartz Friction Vacuum Gauge Using a Self-Oscillating", Jor. of Vacuum Sci. Technology, pp. 2393–2396, 1987.
Ono et al., "Design and Perform. of a Quartz Oscillator Vacuum Gauge with a Controller" Jor. of Vacuum Sci. Tech., pp. 1746–1749, 1985.
Kokubun et al., "Freq. Depend. of a Quartz Oscillator on Gas Pressure", Jor. of Vacuum Sci. Tech., pp. 2184–2187, 1985.
Kokubun et al., "Size Effect of a Quartz Oscillator on its Charact. as a Friction Vacuum Gauge", Jor. of Vacuum Sci. Tech., pp. 1742–1745, 1985.
Pearman, "Low-Cost Gas BTU Meter Using Phys. Prop. Meaure.", Phase III Final Report, Gas Research Instit., 1984.
Clingman et al., "Energy Flowmeter Devel.", Phase I–Gas Samp. Meth., Phase II–Prototype Energy Flowmeter, Gas Research Inst. Annual Report, 1983.
Guozhen et al., "Measur. of Viscosity and Density by a Vibrat. Sphere", Review of Sci. Instru. vol. 56, pp. 1639–1642, 1985.
Chung, "A Linear Oscillatory Viscometer", Review of Scientific Instruments, vol. 56, pp. 1669 and 1670, 1985.
Gast, "Sensors with Oscillating Elements", J. Phys. E: Sci. Instrum., vol. 18, pp. 783–789, 1985.

*Primary Examiner*—Hezron E. Williams
*Assistant Examiner*—Joseph W. Roskos
*Attorney, Agent, or Firm*—Heslin & Rothenberg

[57] ABSTRACT

Transducer apparatus and related method are described for substantially simultaneously determining pressure and one other property (or property combination) of a flowing gas of varying pressure and composition. The technique utilizes several empirical algorithms for correlating the frequency and series resistance of a crystal resonator exposed to the test gas with the desired properties. The apparatus and method can be readily incorporated into an on-line heating value determination process such as that set forth in the referenced co-filed application.

16 Claims, 5 Drawing Sheets fig. 1A fig. 1B fig. 2 fig. 3 fig. 4 fig. 5

MULTIPLE GAS PROPERTY SENSOR

BACKGROUND OF THE INVENTION

1. Technical Field

The present invention relates to instruments and methods for determining properties of a gas and, more particularly, to a transducer apparatus and a related method for substantially simultaneously determining pressure and one other property (or property combination) of a flowing gas of varying pressure and composition.

2. Description of the Prior Art

The heating value of a gaseous substance is of significant interest because it forms one basis for determining the commercial value of that substance as a fuel. Techniques for measuring the quality of gaseous fuels to ascertain the amount of heat available therefrom are already being used in practice for numerous purposes. One particularly novel technique for determining the heating value of a gaseous fuel is described in co-filed U.S. Patent Application entitled "On-Line Combustionless Measurement and/or Regulation of Gaseous Fuels Fed to Gas Consumption Devices," Ser. No. 07/781,598. In addition to determining heating value of a gaseous fuel based upon parameters such as gas density, thermal conductivity, specific heat, molecular weight, viscosity, etc., proper heating value determination normally requires contemporaneous pressure and temperature sensing for correction of the calculated value to standard conditions. Most, if not all, known techniques for determining such gas parameters as pressure and temperature separately measure each desired property. Further, existing sensing devices are often expensive and complex, requiring extensive electronic support equipment and thus warranting only limited use in complex systems where cost is less critical. Fuel gas quality measurement is further complicated by the fact that combustion gases, and particularly natural gases, are typically distributed together notwithstanding separate origin, composition and properties that differ to a greater or lesser extent from each other.

As an example of the most relevant art, it has been known for some time that a vibratory element, such as a quartz crystal, when exposed to a gas will change its frequency of vibration as the gas pressure changes (see, for example, U.S. Pat. No. 4,644,803 and references cited therein). In addition, references exist in the open literature for determining gas density through frequency shift of an oscillator exposed to a test gas (see, e.g., U.S. Pat. No. 4,734,609). However, along with being inoperable in a changing gas pressure and/or changing gas composition environment, most or all of these devices determine only one gas property such as density or pressure.

Thus, a novel, noncomplex approach to the simultaneous measurement of multiple fuel gas properties has clear advantages over the known art, particularly when implemented in a heating value measurement device such as that described in the referenced co-pending application.

SUMMARY OF THE INVENTION

Accordingly, a primary object of the invention is to provide a transducer apparatus and method for determining multiple properties of a gas of varying pressure and composition.

Another object of the present invention is to provide such an apparatus and method which are capable of determining multiple gas properties within the same measurement cycle.

Yet another object of the present invention is to provide such an apparatus and method which are less complex and costly to implement than presently available instruments for determining gas properties.

But another object of the present invention is to provide such an apparatus and method which can be readily incorporated into a heat content measuring apparatus and method.

A further object of the present invention is to provide such an apparatus and method which can be implemented in an on-line manner.

A still further object of the present invention is to provide such an apparatus and method which are capable of determining gas pressure and the property combination (molecular weight $\times$ viscosity) substantially simultaneously.

These and other objects of the present invention are accomplished in one aspect by a transducer apparatus which determines pressure and at least one other gas property or property combination of a test gas of varying pressure, density and viscosity. The apparatus includes a reference vibrator sealed within a chamber having a fixed gas pressure and density, and a detector vibrator exposed to the test gas surrounding the transducer. The frequencies of the reference and detector oscillators are compared by a first means which produces an output signal proportional to the difference in the frequencies of the oscillators. The series resistances of the reference and detector vibrators are compared by a second means which similarly produces an output signal proportional to the difference in the series resistances of the vibrators. Lastly, the transducer apparatus includes computational means for deriving signals representive of test gas pressure and one other gas property based upon the proportional differential frequency signal and the proportional differential series resistance signal obtained from the reference and detector vibrators. In a specific embodiment, the test gas comprises natural gas and the apparatus simultaneously determines pressure and at least one other gas property, which may consist of the property combination (molecular weight $\times$ viscosity).

In another aspect, the present invention comprises a related method for determining two properties of a test gas having varying pressure and composition. The method includes the steps of: providing a reference vibrator sealed within a chamber having a fixed gas pressure and density; providing a detector vibrator exposed to the test gas; causing the reference vibrator and the detector vibrator to vibrate at a resonant frequency, the frequency of the detector oscillator varying with variations in test gas pressure and composition; providing signals corresponding to the frequencies of oscillation of the reference and detector oscillators; comparing the frequencies of the corresponding signals and producing an output signal proportional to the difference in said frequencies; determining the series resistance of the reference vibrator and the series resistance of the detector vibrator; comparing the series resistances of the reference and detector vibrators and producing an output signal proportional to the difference in the series resistances; and deriving signals representative of two gas properties based upon the proportional differential frequency signal and the proportional differential series resistance signal produced from the reference and detector vibrators.

A further feature of the method includes the substantially simultaneous comparison of the frequencies and series resistances of the vibrators to determine the two test gas properties within the same measurement cycle. Again, in one typical implementation the test gas comprises natural gas and the two properties determined are pressure and the property combination (molecular weight × viscosity).

BRIEF DESCRIPTION OF THE DRAWINGS

The subject matter which is regarded as the invention is particularly pointed out and distinctly claimed in the concluding portion of the specification. The invention, however, both as to organization and method of practice, together with further objects and advantages thereof, may best be understood by reference to the following detailed description taken in connection with the accompanying drawings in which:

DETAILED DESCRIPTION OF THE INVENTION

As briefly noted above, the heating value of a gaseous substance is important to determination of the commercial value of that substance as a fuel. In industrial heating processes, it is frequently necessary to feed a well defined amount of heat per unit of time to a furnace in order to obtain optimum results. In other cases, it is desirable to optimize the consumption of fuel, i.e., to feed only the amount of heat actually required by a process even if supplying a larger amount of heat does not adversely affect the process or product. For accounting purposes, billing on the basis of the amount of heat supplied has also been preferred to billing on a volume basis.

A principal goal of the referenced co-filed U.S. patent application entitled "On-Line Combustionless Measurement and/or Regulation of Gaseous Fuels Fed to Gas Consumption Devices" comprises the production of a low cost, reliable and inexpensive meter for determining heating value of gaseous fuel, and particularly natural gas. Such a low cost meter could be installed on-site with most industrial and commercial consumers, and possibly even residential consumers, to more accurately determine heat content of the gas. Due to the complexities involved with available equipment, gas properties and heating value (e.g., BTU/ft$^3$) are presently evaluated only at gas transfer stations.

In one preferred embodiment of the referenced co-pending application a heating value determination method and apparatus is described which utilizes the surprising discovery that heat content of a gaseous fuel can be readily and accurately determined from an empirical expression, for example, of the form:

$$\mu = a_o + b_1\{f(n)(z)\}^{o1} + c_1 f_1(k_{t1}, k_{t2})^{m1} + c_2 f_2(k_{t1}, k_{t2})^{m2} + d_1 c_{pt1}^{p1} \quad (1)$$

where:
$\mu$ = gas heat content;
$a_o$, $b_1$, $c_1$, $c_2$, $d_1$ = constants;
o1, m1, m2, p1 = exponents;
n = viscosity;
z = molecular weight, M, or density, of the fuel gas;
$k_{t1}$ = thermal conductivity at a first temperature, t1;
$k_{t2}$ = thermal conductivity at a second temperature, t2; and
$c_{pt1}$ = specific heat at the first temperature, t1.

Further, as discussed in said co-filed application, where the fuel gas comprises natural gas the preferred algorithm for calculating heat content of the fuel gas reduces to:

$$H_c = -1287.7 + 808,700 C_p^{.73846} - 1,048,800 k^{-1.7142} - 0.00090189(Mn)^{1.7514} \quad (2)$$

where:
$c_p$ = specific heat of the fuel gas;
k = gas thermal conductivity; and
Mn = (molecular weight of the gas) × (viscosity of the gas).

The term molecular weight multiplied by viscosity, Mn, or its alternate expression density multiplied by viscosity, $\rho n$, is capable of being determined by those skilled in the art using a combination of available technologies. However, as noted above, all of these technologies have associated drawbacks, for example: requiring trained personnel to operate, producing time delayed results, lacking repeatability, destroying the sample, being cumbersome or expensive to implement, being incapable of implementation in an on-line manner, and lacking sufficient accuracy due to an inability to completely distinguish constituents. The present invention is designed to avoid these drawbacks by providing a more efficient, inexpensive, reliable and accurate means than any known technique for determining properties of gases, such as gas pressure and the property combination (molecular weight × viscosity), and thereby facilitate the determination of gas heating value.

In a preferred embodiment, the present transducer apparatus and method use a tuning fork type quartz crystal vibrator. The properties of such a mechanically oscillating member depend in part on the viscosity and density of the ambient gas surrounding the member. In particular, the adjacent mass of the ambient gas affects the total mass of the oscillating member, and thereby it s oscillation frequency. Gas density and the viscosity of the gas will affect the Q or equivalent series resistance of the oscillating member. At resonance, its series resistance and frequency are found to be uniquely dependent on the pressure, density, and viscosity of several test gases, such as natural gas, methane, air and others. The apparatus and method of the present invention make use of this relationship.

Figure 1A:
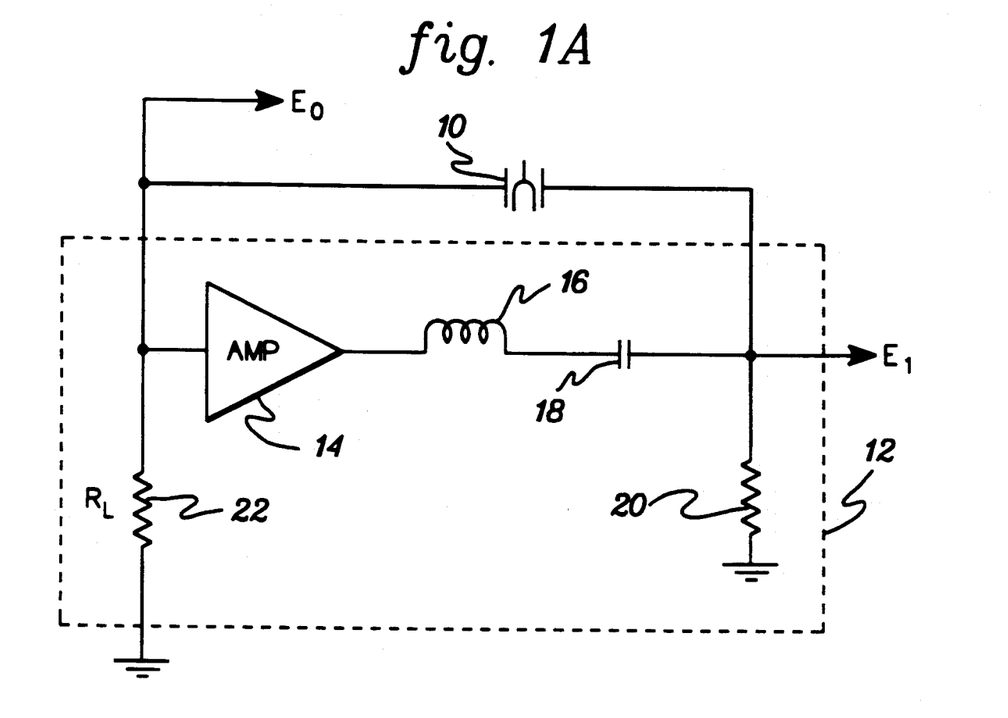
FIG. 1A is a schematic diagram of a tuning fork type crystal vibrator and a basic drive circuit.

Referring now to FIG. 1A, a tuning fork quartz crystal 10 is schematically shown along with a basic drive circuit 12 configured to sustain crystal 10 in oscillation at the crystal resonant frequency. Any available oscillating means, including noncrystalline members such as vibrating plates or membranes, could be substituted for the tuning fork type crystal 10. Ideally, however, a tuning fork oscillator is used because of its low cost, reliability, ready availability and relative insensitivity to temperature variations. Further, although any one of longitudinal, transverse and shear modes of deformation are acceptable for coupling the mechanical oscillator to the test gas, results obtained with shear mode coupling appear superior, particularly when viscosity is one of the gas properties desired. Also, as a result of extensive experimentation, a fundamental oscillation frequency of 160 kHz seems to provide superior coupling of energy between the tuning fork oscillator and the surrounding natural gas, and therefore provides greater accuracy.

Basic drive circuitry 12 includes: an operational amplifier 14, configured with gain; an inductor 16, a capacitor 18 and a resistor 20, all designed to drive crystal 10 with a sine wave; and a load resistance 22 at the input to amplifier 14. The output voltage $E_o$ from crystal 10 is provided as positive feedback to circuit 12 as shown. Voltage $E_o$ varies in value as a function of gas pressure and gas composition surrounding crystal 10.

Figure 1B:
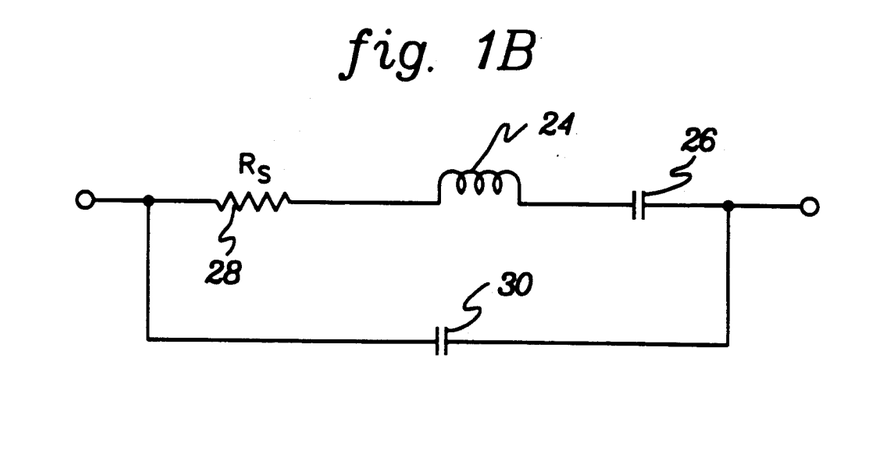
FIG. 1B is a schematic diagram of an equivalent circuit for the tuning fork crystal of FIG. 1A.

FIG. 1B is a schematic diagram of an equivalent electrical circuit for tuning fork type crystal 10. The circuit includes an inductor 24 in series with a capacitance 26 and a resistance 28, all of which are shunted by a capacitance 30. The motional resistance of the test gas to the motion of the tuning fork while oscillating is represented by series resistor 28, $R_s$, which comprises a variable resistance. A small part of $R_s$ represents internal resistive losses within the quartz material that the tuning fork is made of. Determination of series resistance $R_s$ is important to the present apparatus and method.

As described below, two substantially identical tuning fork crystals are used in implementing the preferred transducer apparatus. One crystal is directly exposed to the test gas ambient (i.e., the crystal in the detector oscillator) and the other crystal is sealed in a fixed ambient reference chamber, which is exposed to the test gas ambient (i.e., the crystal in the reference oscillator). The reference oscillator is used to account for effects of temperature variations on detector oscillator readings. The reference chamber is preferably substantially evacuated. The damping component, or series resistance of each tuning fork can be obtained by dividing the voltage across the tuning fork by the current through it at series resonance. Lastly, each tuning fork will control the frequency of its respective oscillator circuit.

Applicant has discovered that with such oscillators a simple relation exists between crystal series resistance and oscillator frequency shift parameters on the one hand and absolute pressure, density or molecular weight, and viscosity on the other. By applying linear progression analysis to experimental results, the following formulas are obtained:

$$P = ((R_{sr} - R_s)/A)^{d/g} \times (B/(f_r - f))^{b/g} \quad (3)$$

$$Zn = ((R_{sr} - R_s)/A)^{c/g} \times (B/(f_r - f))^{a/g} \quad (4)$$

where:
P = gas pressure;
Zn = gas (Z)·(viscosity), where Z = density or molecular weight;
A, B = coefficients;
a, b, c and d = exponents;
g = bc − ad
$R_{sr}$ = series resistance of reference vibrator;
$R_s$ = series resistance of detector vibrator;
$f_r$ = frequency of reference oscillator;
f = frequency of detector oscillator.

Thus, from two simultaneous measurements of a pair of quartz crystals it is possible to determine both gas pressure and the property combination (molecular weight × viscosity) or the property combination (density × viscosity). Series resonance resistance $R_s$ of the detector crystal and series resonance resistance $R_{sr}$ of the reference crystal can be determined from equations of the form:

$$R_s = R_l(1 - E_o/E_i)/(E_o/E_i) \quad (5)$$

$$R_{sr} = R_{lr}(1 - E_{or}/E_{ir})/(E_{or}/E_{ir}) \quad (6)$$

where:
$R_l$ = crystal load resistance of oscillator circuit;
$E_o$ = output voltage of detector crystal;
$E_i$ = oscillator input voltage to detector crystal;
$R_{lr}$ = crystal load resistance of reference oscillator;
$E_{or}$ = output voltage of reference crystal;
$E_{ir}$ = oscillator input voltage to reference crystal.

If the test gas under evaluation comprises natural gas and the crystals used in the transducer apparatus have series resonant frequencies of approximately 160 kHz, then specific values for the coefficients and exponents of equations (3) and (4) are:
A = 0.0038987
B = −1.1992 × 10$^{-6}$
a = 0.64677
b = 1.9498
c = 1
d = 0.8794
g = 1.38103.

Once determined, the property combination Mn can be used in a heating value algorithm such as equation (2) to calculate heat content of the fuel gas, while the pressure of the gas can be used as a conversion factor to translate the calculated heat content to a corresponding value at standard pressure.

Figure 2:
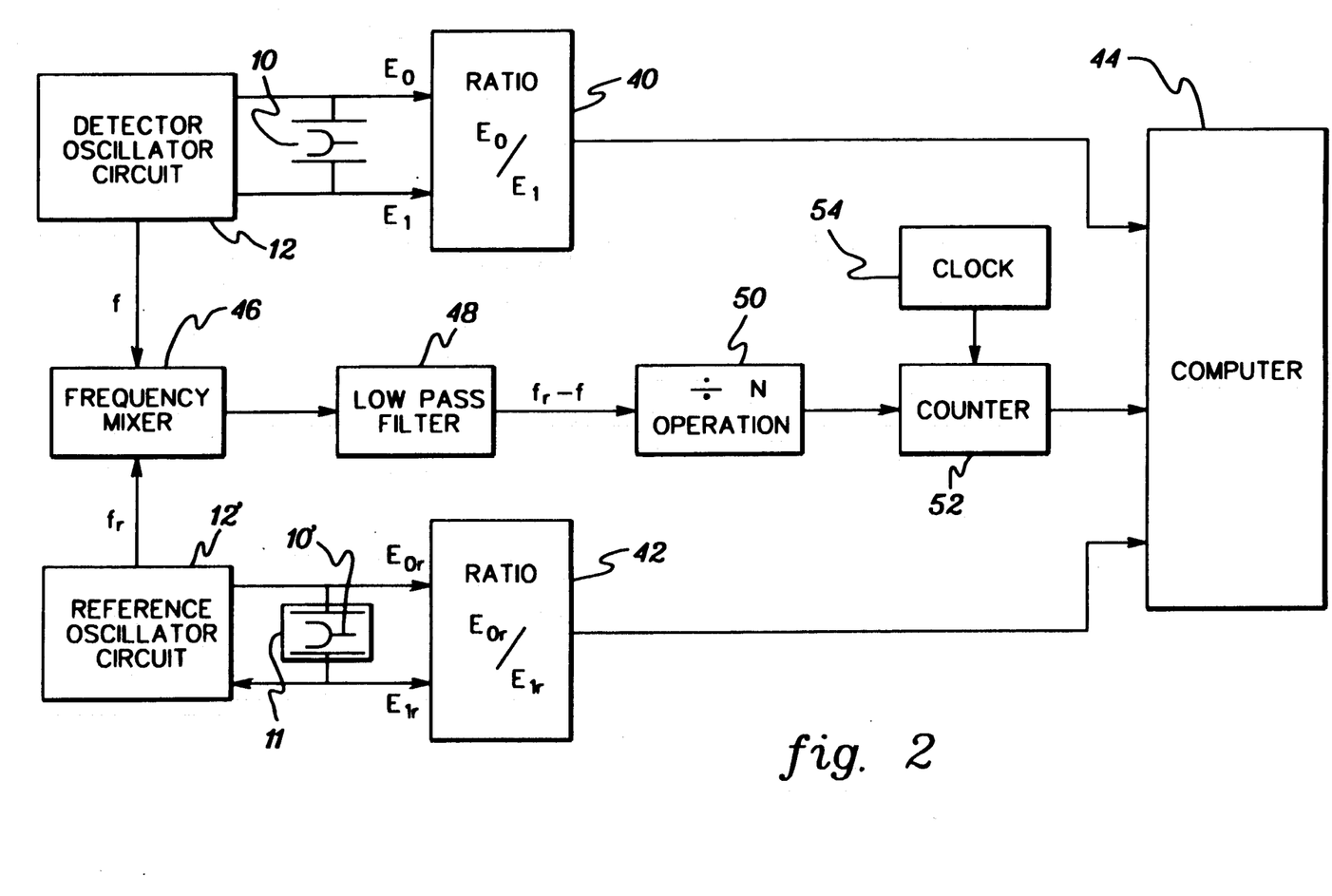
FIG. 2 is a block diagram of a gas property transducer apparatus according to the present invention.

One preferred implementation of the present transducer apparatus is schematically depicted in FIG. 2. In this embodiment, a first tuning fork quartz crystal 10 (herein referred to as the detector crystal) is exposed to the test gas and a second, identical tuning fork quartz crystal 10' (herein referred to as the reference crystal) is positioned within a sealed chamber 11. Sealed chamber 11 is itself exposed to the test gas. The crystals (and chamber 11) preferably reside in a sensor chamber filled with the test gas, such as that described in the referenced co-pending application. Crystals 10 and 10' are sustained in oscillation by detector circuit 12 and reference circuit 12', respectively. The voltages from crystal 10, i.e., output voltage $E_0$ and input voltage $E_i$ are fed through a servo ratioing type of A/D converter, which converts the ac $E_0$ and $E_i$ signals to digital signals and outputs the ratio $E_o/E_i$ 40 to computer 44, (discussed further below with reference to FIG. 5). Computer 44 uses the ratio $E_o/E_i$ to calculate the series resistance $R_s$ of crystal 10, by means of equation (5). Similarly, the output and input voltages $E_{or}$ and $E_{ir}$ from reference crystal 10' are fed to A/D converter 42 for conversion to digital format and determination of the ratio $E_{or}/E_{ir}$. Computer 44 uses the ratio $E_{or}/E_{ir}$ to calculate the series resistance $R_{sr}$ of crystal 10' by means of equation (6).

Simultaneous with this signal processing, frequency signals are fed from detector oscillator circuit 12 and reference oscillator circuit 12' to a frequency mixer 46

(discussed below) which is configured to output the sum and difference frequencies between oscillator circuits 12 and 12'. Alternatively, frequency signals from the oscillators could be fed, with subsequent appropriate conversion, directly to computer 44 for direct computer calculation of the difference in the oscillator circuit frequencies ($f_r-f$). From the output of mixer 46, the signals are fed through a low pass filter 48, which eliminates the unwanted summation frequency; thereafter, the difference in frequencies ($f_r-f$) is fed to a divide by N operation 50. Operation 50 comprises an optional and arbitrary division of the frequency difference signal $f_r-f$ by a preselected number N to reduce the frequency of the difference signal and improve its compatibility with other system components. The reduced difference signal is then fed to a counter 52 which determines, for example, the number of pulses from a clock 54 that occur within one cycle of the difference signal. A representative signal is output from counter 52 to computer 44 for determination of the desired multiple gas properties, e.g., pursuant to equations (3) and (4).

Figure 3:
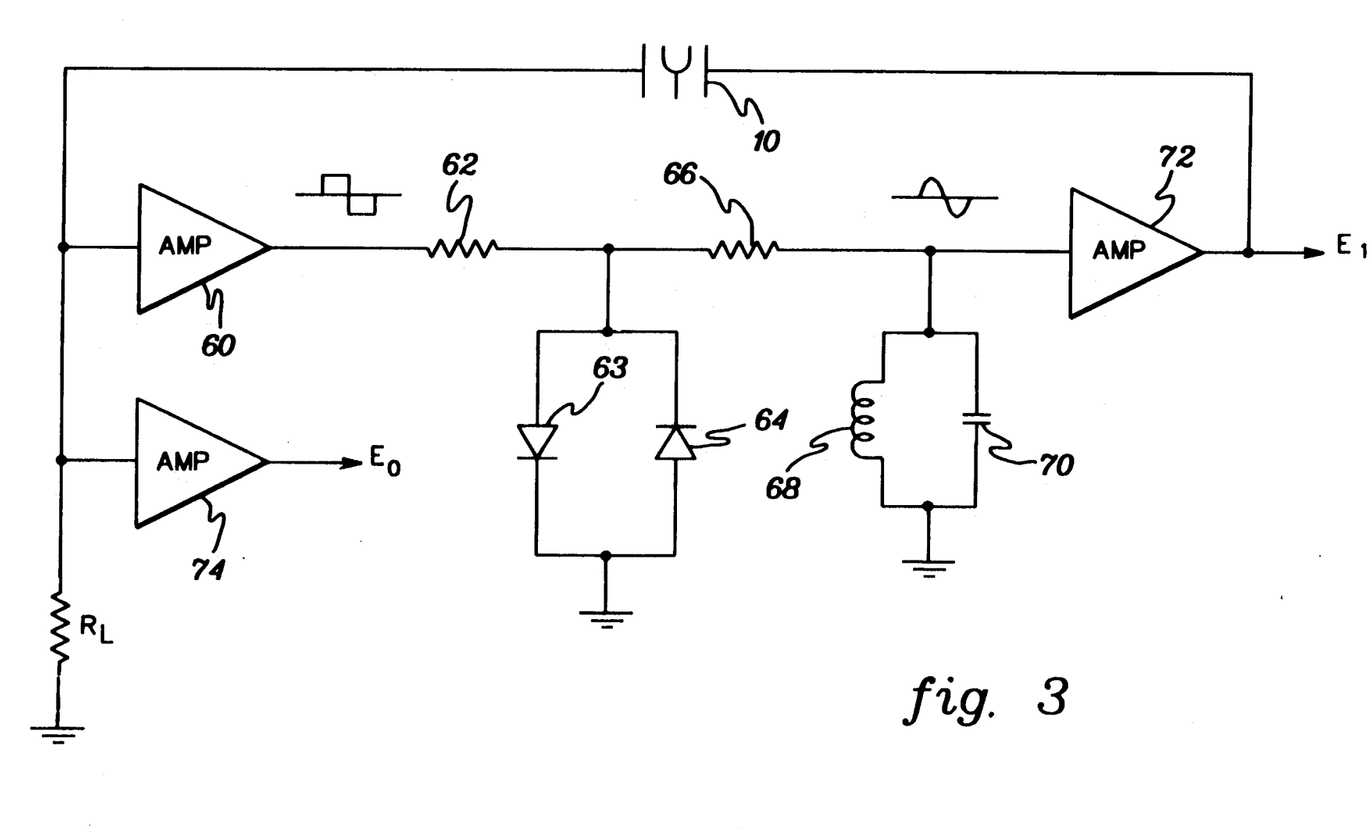
FIG. 3 is a schematic diagram of a preferred drive circuit for the detector and reference vibrators of FIG. 2.

FIG. 3 is a schematic diagram of a preferred embodiment of detector oscillator circuit 12 and reference oscillator circuit 12'. (Since the implementation is identical for both the detector and reference circuits, only the detector circuit 12 is described in detail herein.) As shown, input voltage $E_i$ is fed to tuning fork type crystal 10. Output voltage $E_o$ from crystal 10 is fed back to the drive circuitry at the input of an amplifier 60, which comprises a cascode amplifier configured with gain. In normal operation, amplifier 60 is overloaded such that an approximate square wave signal appears at its output. This square wave signal is fed through a first series resistor 62 to a pair of shunt diodes 63 and 64, which are configured as an amplitude clamp to provide a constant amplitude for driving the crystal. A second series resistor 66 is disposed between the amplitude clamp and an LC resonant circuit comprised as an inductor 68 and a capacitor 70. The LC resonant circuit is tuned to the same frequency as the oscillator and functions to convert the square wave signal from amplifier 60 to a sine wave signal. A sine wave is preferred for driving crystal 10 to facilitate accurate determination of the equivalent series resistance $R_s$ pursuant to equation (5), i.e., since $E_o$ is a sine wave, preferably $E_i$ is also. Subsequent the LC resonant circuitry, a second amplifier 72, this one without gain, is used as an impedance conversion device. Amplifier 72 comprises an emitter follower with a low output impedance and high input impedance. Similarly, an amplifier 74 is disposed at the output of crystal 10 for measuring output voltage $E_o$ across the load resistor $R_l$ without loading the resistor. Output voltage $E_o$ and input voltage $E_i$ are separately fed to ratio $E_o/E_i$ 40 circuitry (FIG. 2).

Figure 4:
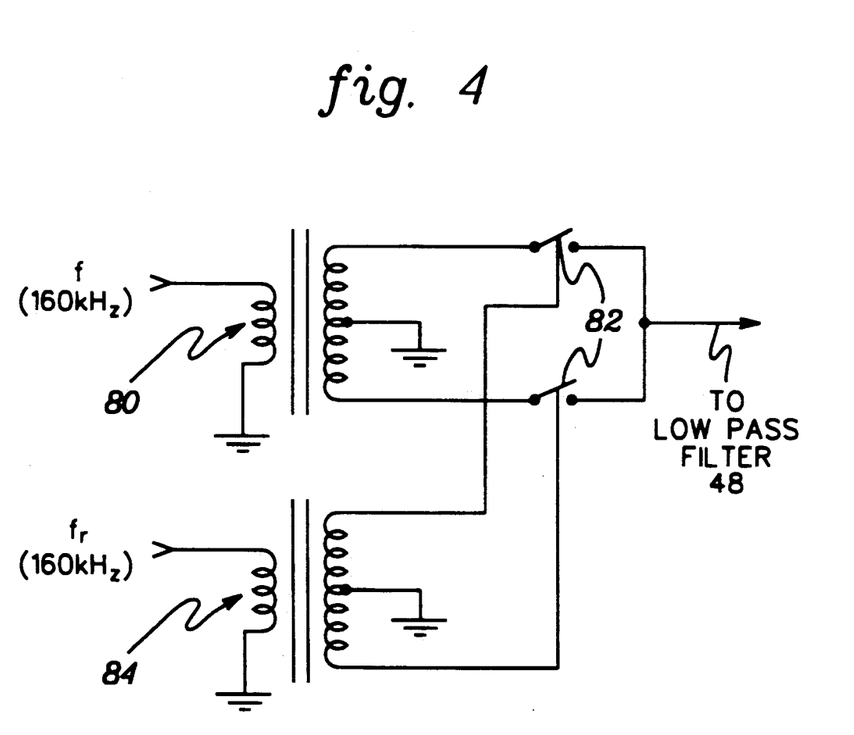
FIG. 4 is a schematic diagram of an equivalent circuit for the frequency mixer of FIG. 2.

Since the frequencies of both input voltage $E_i$ and output voltage $E_o$ are the same, the frequencies fed to frequency mixer 46 (FIG. 2) can be derived from either voltage signal. An equivalent circuit representation for frequency mixer 46 is depicted in FIG. 4. This circuit comprises a balanced frequency mixer (such as those available in the open literature) which obtains, in part, a difference between the detector oscillator frequency f and the reference oscillator frequency $f_r$. The detector oscillator frequency f is fed to the primary windings of a first transformer 80 which has a center tapped secondary winding. Because crystal 10 is exposed to the test gas, e.g., natural gas, the exact frequency of detector oscillator circuit 12 will vary with the pressure and composition of the surrounding gas such that it will be slightly off from 160 kHz (i.e., the resonant frequency of the reference oscillator). The voltages at opposite sides of the secondary winding of transformer 80 are 180° out of phase. Switches 82, for example, field effect transistors, are closed and opened in synchronism with the phase of the reference oscillator frequency $f_r$. Frequency $f_r$ is fed into the primary winding of a second transformer 84 which also has a center tapped secondary winding. The effect of such a circuit is to multiply the two input frequencies together such that a sum and a difference signal are attained as outputs. Since the unwanted sum signal comprises a much higher frequency than the difference signal, it is filtered out by a subsequent low pass filter 48 (FIG. 2).

Figure 5:
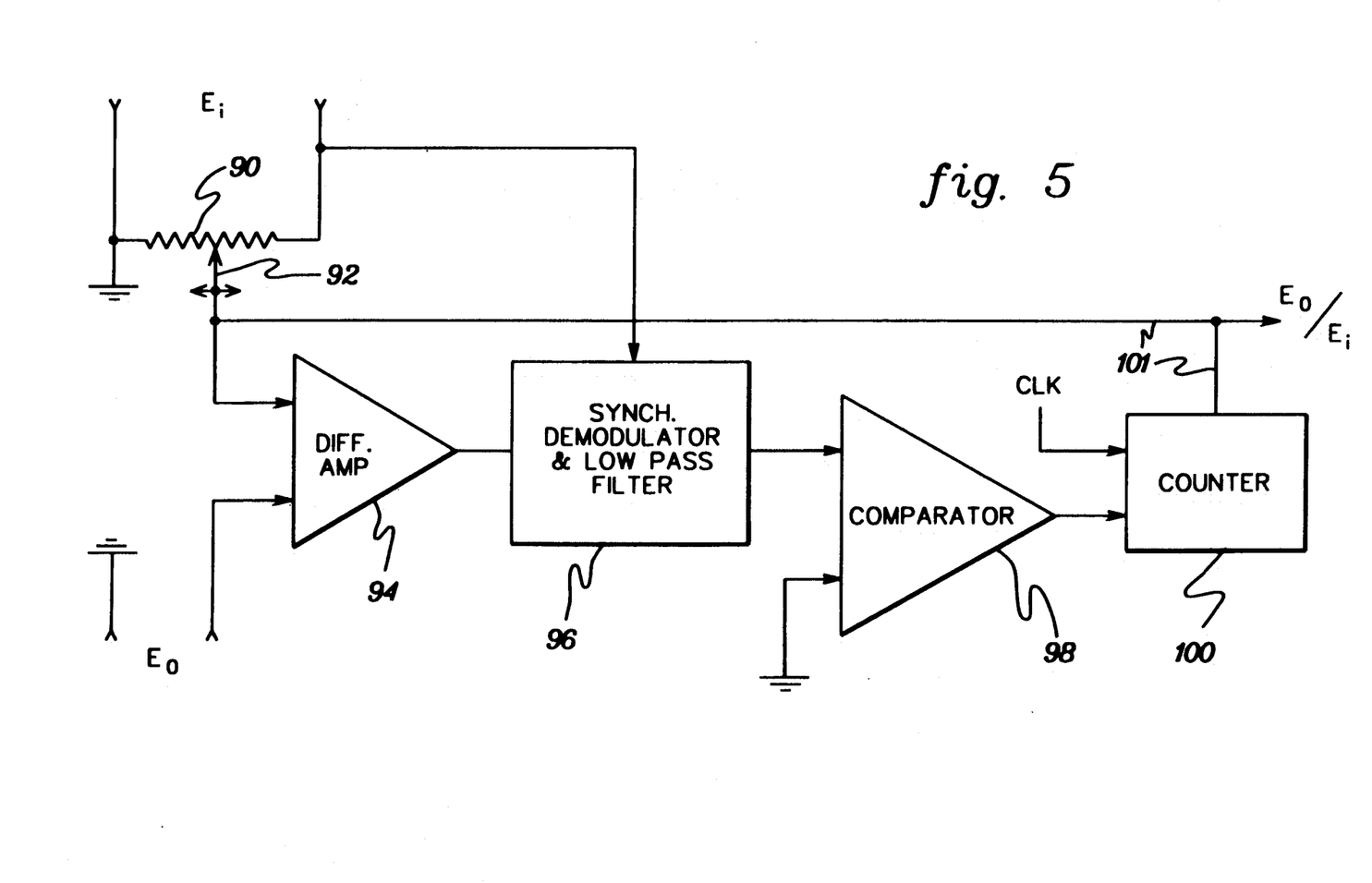
FIG. 5 is a schematic diagram of the ratioing circuits of FIG. 2.

One implementation for the ratio $E_o/E_i$ 40 circuitry is depicted in FIG. 5. (Again ratio $E_o/E_i$ 42 circuit would be identical.) This circuit comprises a servo ratioing type A/D converter, specific details of which are available in the open literature. The circuit uses a very accurate resistance divider string in a D/A converter for measuring the actual signal ratio $E_o/E_i$ with a closed loop servo continuously driving the ratio device to null. The ratio output is digital by taking advantage of the digital drive in a D/A converter which is used backwards as an A/D readout. This approach to determining the ratio $E_o/E_i$ is more accurate because it is independent of the relative oscillator signal amplitudes, and is a bridge ratio concept involving the use of $R_s$ and $R_l$ as two bridge arms against the D/A resistor string (i.e. the other two bridge arms).

Briefly explained, a variable potentiometer or resistance string 90 receives input voltage $E_i$. Potentiometer 90 includes a wiper 92 which traverses the resistor string to define a voltage proportional to input voltage $E_i$. This proportional voltage is fed to a differential amplifier 94 which compares the proportional signal to output voltage $E_o$. The output of amplifier 94 is fed to a combined synchronous demodulator and low pass filter 96 which converts the sine wave differential input signal to a dc voltage and hence to a comparator 98 which determines whether the resulting voltage signal is positive or negative. The output of comparator 98 is fed to a counter 100 which receives, for example, a 10 MHz clock input signal for counting. The output of comparator 98 directs the counter to either increase or decrease its pulse count. The output of counter 100 is fed via line 101 back to wiper 92. The feedback circuitry continuously operates to drive wiper 92 to null whereupon the voltage signal taken from the resistance string is equal to output voltage $E_o$. Once nulled, the resulting ratio $E_o/E_i$ signal 101 is fed to computer 44 (FIG. 2) for use in equations (5) and (6).

Along with the transducer apparatus, the invention comprises the generalized method for determining multiple properties of a test gas having varying pressure and composition as set forth above. In particular, the method includes the steps of: causing a reference vibrator and a detector vibrator to vibrate at a resonancy frequency, whereby the frequency of the detector vibrator (exposed to the test gas) varies with variations in the gas pressure and composition; deriving frequency signals corresponding to the frequencies of oscillation of the reference vibrator and the detector vibrator; comparing the corresponding frequency signals and producing an output signal proportional to the difference in their frequencies; determining the series resistance of the reference vibrator and the series resistance of the detector vibrators; comparing the series resistances of the two oscillators and producing a signal proportional to the difference in their series resistances; and deriving signals representative of two gas properties based upon the proportional differential frequency signal and the proportional differential series resistance signal produced from the reference and detector vibrators. The two properties determined can comprise pressure and the property combination (molecular weight × viscosity), which are determinable by equations (3) and (4). Preferably, the two comparing steps, i.e., comparing the frequencies and comparing the series resistances occur substantially simultaneously such that the two properties of the test gas are derived in the same measurement cycle.

While the invention has been described in detail herein in accordance with certain preferred embodiments thereof, many modifications and changes therein may be affected by those skilled in the art. Accordingly, it is intended by the appended claims to cover all such modifications and changes as fall within the true spirit and scope of the invention.

What is claimed is:

1. Transducer apparatus capable of determining pressure and at least one other property of a test gas, said apparatus comprising:
   a reference vibrator sealed within a chamber having a fixed gas pressure and density;
   a detector vibrator exposed to the test gas surrounding the transducer;
   first means for comparing the frequencies of said reference and detector vibrators and for producing a signal proportional to the difference in the frequencies of said vibrators;
   second means for comparing the series resistances of said reference and detector vibrators and for producing a signal proportional to the difference in the series resistances of said vibrators; and
   means for deriving signals representative of gas pressure and one other property of said test gas based upon said proportional differential frequency signal and said proportional differential series resistance signal produced from said reference and detector vibrators.

2. The transducer apparatus of claim 1, wherein said second comparing means operates substantially simultaneously with said first comparing means such that the transducer apparatus determines test gas pressure and at least one other property of the test gas substantially simultaneously.

3. The transducer apparatus of claim 1, wherein said at least one other property comprises the property combination (molecular weight × viscosity).

4. The transducer apparatus of claim 3, wherein said test gas comprises a fuel gas.

5. The transducer apparatus of claim 4, wherein said signal deriving means produces signals representative of fuel gas pressure and fuel gas (molecular weight × viscosity) according to the formulas:

$$P = ((R_{sr} - R_s)/A)^{d/g} \times (B/(f_r - f))^{b/g}$$

$$Mn = ((R_{sr} - R_s)/A)^{c/g} \times (B/(f_r - f))^{a/g}$$

where:
P = gas pressure;
Mn = gas (molecular weight × viscosity);
A, B = coefficients;
a, b, c and d = exponents;
g = bc − ad;
$R_{sr}$ = series resistance of reference vibrator;
$R_s$ = series resistance of detector vibrator;
$f_r$ = frequency of reference oscillator;
f = frequency of detector oscillator.

6. The transducer apparatus of claim 5, wherein the series resistance of said detector vibrator, $R_s$, and the series resistance of said reference vibrator, $R_{sr}$, are determined according to the formulas:

$$R_s = R_l(1 - E_o/E_i)/(E_o/E_i)$$

$$R_{sr} = R_{lr}(1 - E_{or}/E_{ir})/(E_{or}/E_{ir})$$

where:
$R_l$ = vibrator load resistance of detector oscillator
$E_o$ = output voltage of detector vibrator
$E_i$ = input voltage to detector vibrator
$R_{lr}$ = vibrator load resistance of reference oscillator
$E_{or}$ = output voltage of reference vibrator
$E_{ir}$ = input voltage to reference vibrator.

7. The transducer apparatus of claim 5, wherein said reference vibrator and said detector vibrator operate in the shear deformation mode.

8. The transducer apparatus of claim 7, wherein said reference vibrator and said detector vibrator each comprise a tuning fork crystal.

9. The transducer apparatus of claim 8, wherein the fuel gas comprises natural gas and said crystals have a 160 kHz fundamental resonance frequency and wherein:
A = 0.0038987
B = −1.1992 × 10⁻⁶
a = 0.64677
b = 1.9498
c = 1
d = 0.8794
g = 1.38103.

10. The transducer apparatus of claim 5, wherein said reference vibrator is sealed in a highly evacuated chamber.

11. The transducer apparatus of claim 1, wherein said at least one other property comprises the property combination (density) × (viscosity).

12. The transducer apparatus of claim 11, wherein said test gas comprises a fuel gas and wherein said signal deriving means produces signals representative of fuel gas pressure and the property combination (density) × (viscosity) according to the formulas:

$$P = ((R_{sr} - R_s)/A)^{d/g} \times (B/(f_r - f))^{b/g}$$

$$n = ((R_{sr} - R_s)/A)^{c/g} \times (B/(f_r - f))^{a/g}$$

where:
P = gas pressure;
n = gas (density) × (viscosity);
A, B = coefficients;
a, b, c and d = exponents;
g = bc − ad;
$R_{sr}$ = series resistance of reference vibrator;
$R_s$ = series resistance of detector vibrator;
$f_r$ = frequency of reference oscillator;
f = frequency of detector oscillator.

13. The transducer apparatus of claim 12, wherein said reference vibrator and said detector vibrator operate in the shear deformation mode and each comprise a tuning fork crystal.

14. A method for determining two properties of a test gas having varying pressure and composition, said method comprising the steps of:
  (a) providing a reference vibrator sealed within a chamber having a fixed gas pressure and density, and exposing said chamber to the test gas;
  (b) providing a detector vibrator exposed to the test gas;
  (c) causing each of the reference vibrator and the detector vibrator to vibrate at a resonant frequency, said resonant frequency of the detector vibrator varying with variations in test gas pressure and composition;
  (d) providing frequency signals corresponding to the frequencies of oscillation of the reference vibrator and the detector vibrator;
  (e) comparing said corresponding frequency signals and producing an electrical signal proportional to the difference in said frequencies;
  (f) determining the series resistance of the reference vibrator and the series resistance of the detector vibrator;
  (g) comparing the series resistances of said reference and detector vibrators and producing an electrical signal proportional to the difference in said series resistances; and
  (h) deriving signals representative of two gas properties based upon said proportional differential frequency electrical signal and said proportional differential series resistance electrical signal produced using said reference and detector vibrators.

15. The method of claim 14, wherein said comparing step (e) and said comparing step (g) occur substantially simultaneously such that said two test gas properties are determined within the same measurement cycle.

16. The method of claim 14, wherein the two gas properties determined by said process comprise pressure and the property combination (molecular weight × viscosity) and wherein said deriving step (h) ascertains said signals representative of the two gas properties via the formulas:

$$P = ((R_{sr} - R_s)/A)^{d/g} \times (B/(f_r - f))^{b/g}$$

$$Mn = ((R_{sr} - R_s)/A)^{c/g} \times (B/(f_r - f))^{a/g}$$

where:
  $P$ = gas pressure;
  $Mn$ = gas (molecular weight × viscosity);
  $A, B$ = coefficients;
  $a, b, c$ and $d$ = exponents;
  $g = bc - ad$;
  $R_{sr}$ = series resistance of reference vibrator;
  $R_s$ = series resistance of detector vibrator;
  $f_r$ = frequency of reference oscillator;
  $f$ = frequency of detector oscillator.

* * * * *